(12) United States Patent
Weinberg

(10) Patent No.: US 10,888,243 B2
(45) Date of Patent: Jan. 12, 2021

(54) NON-INVASIVE METHOD FOR FOCAL DEEP-BRAIN STIMULATION EQUIPMENT AND METHODOLOGIES

(71) Applicant: Weinberg Medical Physics, Inc., North Bethesda, MD (US)

(72) Inventor: Irving N. Weinberg, North Bethesda, MD (US)

(73) Assignee: WEINBERG MEDICAL PHYSICS INC, North Bethesda, MD (US)

( * ) Notice: Subject to any disclaimer, the term of this patent is extended or adjusted under 35 U.S.C. 154(b) by 187 days.

(21) Appl. No.: 16/014,072

(22) Filed: Jun. 21, 2018

(65) Prior Publication Data

US 2018/0368726 A1    Dec. 27, 2018

Related U.S. Application Data

(60) Provisional application No. 62/523,539, filed on Jun. 22, 2017.

(51) Int. Cl.
*A61B 5/05* (2006.01)
*A61B 5/00* (2006.01)
*A61B 5/055* (2006.01)
*A61N 1/32* (2006.01)
*A61N 2/00* (2006.01)
(Continued)

(52) U.S. Cl.
CPC .......... *A61B 5/0515* (2013.01); *A61B 5/0042* (2013.01); *A61B 5/055* (2013.01); *A61N 1/0534* (2013.01); *A61N 1/327* (2013.01); *A61N 1/36067* (2013.01); *A61N 1/37205* (2013.01); *A61N 2/006* (2013.01); *A61N 2/02* (2013.01); *H01F 1/0045* (2013.01); *A61N 1/36125* (2013.01); *A61N 1/36128* (2013.01);
(Continued)

(58) Field of Classification Search
CPC ..... A61B 5/0515; A61B 5/0042; A61B 5/055; A61N 1/37514; A61N 1/3756; A61N 2/006; A61N 2/02; A61N 1/0534; A61N 1/36067; A61N 1/36125; A61N 1/36128; A61N 1/37205; A61N 1/37223; A61N 1/327; H01F 1/0045
See application file for complete search history.

(56) References Cited

U.S. PATENT DOCUMENTS 9,380,959 B2   7/2016  Weinberg et al.
9,622,809 B2   4/2017  Weinberg
(Continued)

OTHER PUBLICATIONS

U.S. Appl. No. 62/490,975 entitled "Apparatus and Method for Remote Detection of Electric Fields in Living Tissues Using Magnetic Particles and Liquid Crystals" filed Apr. 27, 2017, 8 pages.
(Continued)

*Primary Examiner* — Christine H Matthews
*Assistant Examiner* — Joshua Daryl D Lannu
(74) *Attorney, Agent, or Firm* — Barnes & Thornburg LLP

(57) ABSTRACT

Disclosed embodiments enable equipment and methodologies that generate a magnetic field using at least one coil under the control of a controller and transduce radio-frequency energy into lower-frequency current or voltage under control of the controller for application to tissue in a subject's body, whereby the transduction produces a lower-field current or voltage that has an effect upon the subject's body tissue.

24 Claims, 4 Drawing Sheets

(51) Int. Cl.
   *A61N 1/372* (2006.01)
   *A61N 1/05* (2006.01)
   *A61N 1/36* (2006.01)
   *H01F 1/00* (2006.01)
   *A61N 2/02* (2006.01)
   *A61N 1/375* (2006.01)

(52) U.S. Cl.
   CPC ........ *A61N 1/3756* (2013.01); *A61N 1/37223* (2013.01); *A61N 1/37514* (2017.08)

(56) References Cited

U.S. PATENT DOCUMENTS

| | | |
|---|---|---|
| 9,694,196 B2 | 7/2017 | Weinberg et al. |
| 2013/0204120 A1 | 8/2013 | Weinberg |
| 2015/0238110 A1* | 8/2015 | Weinberg ............ A61B 5/0515 600/431 |
| 2017/0069416 A9 | 3/2017 | Mair et al. |
| 2017/0227617 A1 | 8/2017 | Weinberg et al. |
| 2017/0265927 A1 | 9/2017 | Weinberg |

OTHER PUBLICATIONS

R. C. Van Lehn et al.; "Free Energy Change for Insertion of Charged, Monolayer-Protected Nanoparticles Into Lipid Bilayers," Soft Matter, vol. 10, No. 4, p. 648, Dec. 2014.

C. L. Kolarcik et al.; "In Vivo Effects of L1 Coating on Inflammation and Neuronal Health at the Electrode-Tissue Interface in Rat Spinal Cord and Dorsal Root Ganglion," Acta Biomater., vol. 8, No. 10, pp. 3561-3575, Oct. 2012.

J. Kuhn et al.; "Deep Brain Stimulation of the Nucleus Accumbens and Its Usefulness in Severe Opioid Addiction," Mol. Psychiatry, vol. 19, No. 2, pp. 145-146, Feb. 2014.

* cited by examiner

NON-INVASIVE METHOD FOR FOCAL DEEP-BRAIN STIMULATION EQUIPMENT AND METHODOLOGIES

CROSS-REFERENCE TO RELATED APPLICATION(S)

This application relies for priority on U.S. Provisional Patent Application Ser. No. 62/523,539, entitled "NON-INVASIVE METHOD FOR FOCAL DEEP-BRAIN STIMULATION," filed on Jun. 22, 2017, the entirety of which being incorporated by reference herein.

FIELD

Disclosed embodiments are directed, generally, to medical therapy, and a brain machine interface that alters and/or diagnoses and or improves biological, cognitive, and/or mood related brain operation.

BACKGROUND

Focal electrical brain stimulation has been shown to be effective in treating various conditions, including Parkinsonism and depression.

SUMMARY

The following presents a simplified summary in order to provide a basic understanding of some aspects of various invention embodiments. The summary is not an extensive overview of the invention. It is neither intended to identify key or critical elements of the invention nor to delineate the scope of the invention. The following summary merely presents some concepts of the invention in a simplified form as a prelude to the more detailed description below.

In accordance with disclosed embodiments, equipment and methodologies generate a magnetic field using at least one coil under the control of a controller and transduce radio-frequency energy into lower-frequency current or voltage under control of the controller for application to tissue in a subject's body, whereby the transduction produces a lower-field current or voltage that has an effect upon the subject's body tissue.

As an overall introduction to this invention, an important concept of the invention is that one or more functional particles (whose function is dependent on a specific electromagnetic frequency when the particles are a magnetic field similar to the Earth's field) may be placed in a specific location in a human subject's body. When a device emitting that specific electromagnetic frequency is near the human subject, the particles have a beneficial effect on the human subject. It is understood that "functional particle" means a particle that has a particular action, for example delivers a drug or applies a voltage or current or moves.

BRIEF DESCRIPTION OF FIGURES

A more complete understanding of the disclosed embodiments and the utility thereof may be acquired by referring to the following description in consideration of the accompanying drawings, in which like reference numbers indicate like features, and wherein.

DETAILED DESCRIPTION

The description of specific embodiments is not intended to be limiting. To the contrary, those skilled in the art should appreciate that there are numerous variations and equivalents that may be employed without departing from the scope of the present invention. Those equivalents and variations are intended to be encompassed by the present invention.

In the following description of various embodiments, reference is made to the accompanying drawings, which form a part hereof, and in which is shown, by way of illustration, various embodiments in which the invention may be practiced. It is to be understood that other embodiments may be utilized and structural and functional modifications may be made without departing from the scope and spirit of the present invention.

Moreover, it should be understood that various connections are set forth between elements in the following description; however, these connections in general, and, unless otherwise specified, may be either direct or indirect, either permanent or transitory, and either dedicated or shared, and that this specification is not intended to be limiting in this respect.

As explained above, focal electrical brain stimulation has been shown to be effective in treating various conditions, including Parkinsonism and depression. Additional indications which have been shown to be effective, include addiction therapy and memory enhancement. Such indications may be more widely or effectively treated with deep brain stimulation provided that a procedure for implanting one or more stimulators within a subject's body, e.g., human subject's body, is less invasive.

Furthermore, future indications may include the potential for fabrication, production and/or manufacture of one or more brain-machine interfaces. In accordance with disclosed embodiments, equipment, e.g., an apparatus and/or system, and a method of implementing deep brain stimulation may be provided and utilized with no or minimal invasiveness with regard to a subject's body.

In accordance with disclosed embodiments, equipment and methodologies for stimulating or otherwise modulating neurons and nerves in tissues in a subject's body are provided. For the purposes of this description, the term "body" refers to the body of a living thing, either an animal or human or plant. For the purposes of this description, the terms "neuron" or "electrically-active cells" refer to any cell or tissue which can be stimulated or affected by the application of electrical charge or voltage.

For the purposes of this description, the term "modulated" or "modulation" or "stimulated" or "stimulation" are intended to include at least the effect of changing or causing the action or response of a neuron, whether for increased firing rate or decreased firing rate. For the purposes of this description, the term "tissue" or "tissues" refers at least to cells or tissues in the body.

Figure 1:
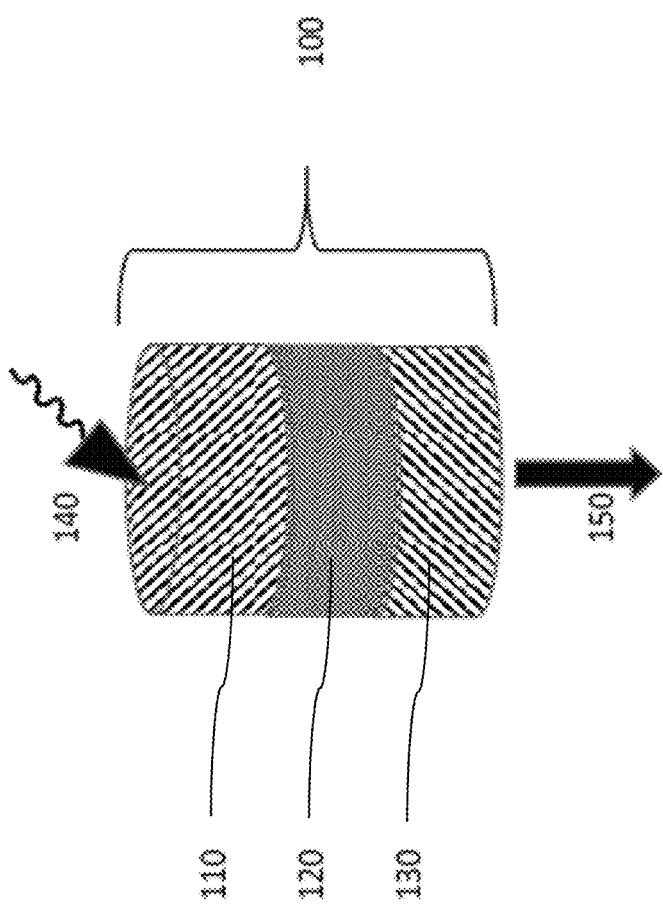
FIG. 1 illustrates an example of a particle used to deliver an electrical charge to a location in a subject's body in accordance with the disclosed embodiments.

FIG. 1 represents an example of particle 100 provided in accordance with the disclosed embodiments for use in delivering electrical charge to a location in an animal or human body. In accordance with at least one embodiment, the particle 100 may be a spintronic device, which polarizes electron spins that pass through the particle.

A spintronic device includes layers (100, 120, 130) of magnetizable and other materials (generally in a sub-micron-sized assembly) which can modulate a current under the influence of applied electromagnetic fields. In FIG. 1, electromagnetic energy 140 (for example in the form of radiofrequency energy) is converted to electrical current 150. The spin of an electron is an angular momentum that is separate from the angular momentum due to its orbital motion. Like orbital angular momentum, the spin has an associated magnetic moment. The spins of many electrons can act together to affect the magnetic and electronic properties of a material. A spintronic particle requires manipulation of spin-polarized electrons to generate a net surplus of spin up or spin down electrons.

Spin Torque Nano-Oscillators (STNOs, also known as spin-valves) are one class of spintronic devices. In an STNO, currents of flowing electrons are polarized as a result of interactions with a magnetic layer. The spin-polarized current can then interact with a second magnetic layer, imparting momentum ("spin-torque") that can drive microwave oscillations of the magnetic orientation of this second magnetic layer. These oscillations may be manipulated and controlled to stimulate tissue in the body using external radiofrequency antennas.

For the purpose of this disclosure, STNOs are presented as one component of one enabling configuration. However, it should be understood that other spintronic particles (e.g., spin vortex) may be used instead of the STNO, or that the classic STNO may be modified in accordance with disclosed embodiments.

An example of the spintronic particle 100 is shown in FIG. 1, in which layer 110 is a material layer (for example gold or copper), 120 is another material through which electrons may pass (for example, permalloy), and layer 130 is another magnetic material (for example copper, gold, or iron). For the purposes of this specification, the term "spintronic" is used as an example to describe any combination of materials that can convert incident electromagnetic or magnetic radiation into electrical current or voltage (i.e., "conversion device"), for example spin vortex devices, or magnetoelectric devices, or small electrical or magnetic circuits and/or circuit elements or radiofrequency identification devices (RFID). It is understood that any such conversion device may be used as part of this invention instead of particle 100.

In accordance with at least one embodiment, at least one particle 100 with magnetically-dependent frequency selectivity is constructed so that, at or near the earth's magnetic field strength, when the at least one particle 100 is exposed to a Radio-Frequency (RF) pulse that the particle is sensitive to, the energy of the RF pulse is converted to an electrical charge, current or voltage that the neuron is stimulated or otherwise modulated. As a result, by positioning this at least one particle 100 near a neuron, and emitting such an RF pulse, the neuron may be stimulated by the resulting electric charge, current or voltage. Further stimulation, likewise, may be controlled by controlling or modulating the RF pulse applied to the at least one particle 100.

As mentioned above, spintronic particle 100 may be selectively sensitive to incident RF energy 140 at a frequency that is dependent on the ambient magnetic field which the particle experiences, similar to the case taught by U.S. Pat. No. 9,622,809, entitled "APPARATUS AND METHOD FOR SPATIALLY SELECTIVE INTERVENTIONAL NEUROPARTCLES" (incorporated by reference in its entirety). The desired selectivity may be implemented through selection of the size and material of components of particle 100.

Another way of implementing frequency selectivity as a function of the ambient magnetic field may be to use magneto-electric or RFID methods, for example, as taught in the U.S. Non-provisional patent application Ser. No. 15/614,061 (U.S. Patent Publication 2017/0265927), entitled "SPATIALLY SELECTIVE INTERVENTIONAL NEUROPARTICLE WITH MAGNETOELECTRIC MATERIAL," (incorporated herein by reference). This alternative method of implementing magnetically-dependent frequency selectivity may not require the particular configuration of materials shown in FIG. 1.

Thus, for the purpose of this description, the particular configuration of FIG. 1 is shown as merely one enabling embodiment, and it should be understood that other types and classes of particles (for example as cited above) are included as part of the disclosed embodiments of the invention.

For the purposes of this disclosure, the at least one particle may be described as a magnetically-dependent RF transducer, in that the frequency of effective transduction of RF energy to low frequency electrical current is dependent on an ambient magnetic field.

Thus, the disclosed embodiments provide the ability to stimulate neurons by implanting at least one particle in a desired location in or near a neuron by applying electromagnetic energy to the particle at a frequency to which the particle is most sensitive. This enables conversion of the electromagnetic energy to electrical charge, current or voltage so that the neuron is stimulated or otherwise modulated at or near the earth's magnetic field.

The particle efficiency of transduction may be maximal at the Earth's field, for example at least 10% higher when the patient is exposed to the Earth's magnetic field as when the patient is exposed to a magnetic field that is twice as high or twice as low as the Earth's magnetic field. This frequency-dependent efficiency may be implemented through judicious selection of materials, configuration, and dimensions of materials in the particle, for example as is well known for spintronic devices. For the purposes of this specification, Earth's field is defined as a magnetic field whose magnitude is between 25 to 65 microteslas.

As shown in FIG. 1, an RF electromagnetic wave 140 is shown entering one of the magnetic layers 110, 130, and being converted into an electrical current 150, which has a lower frequency than incident wave 140.

Figure 2:
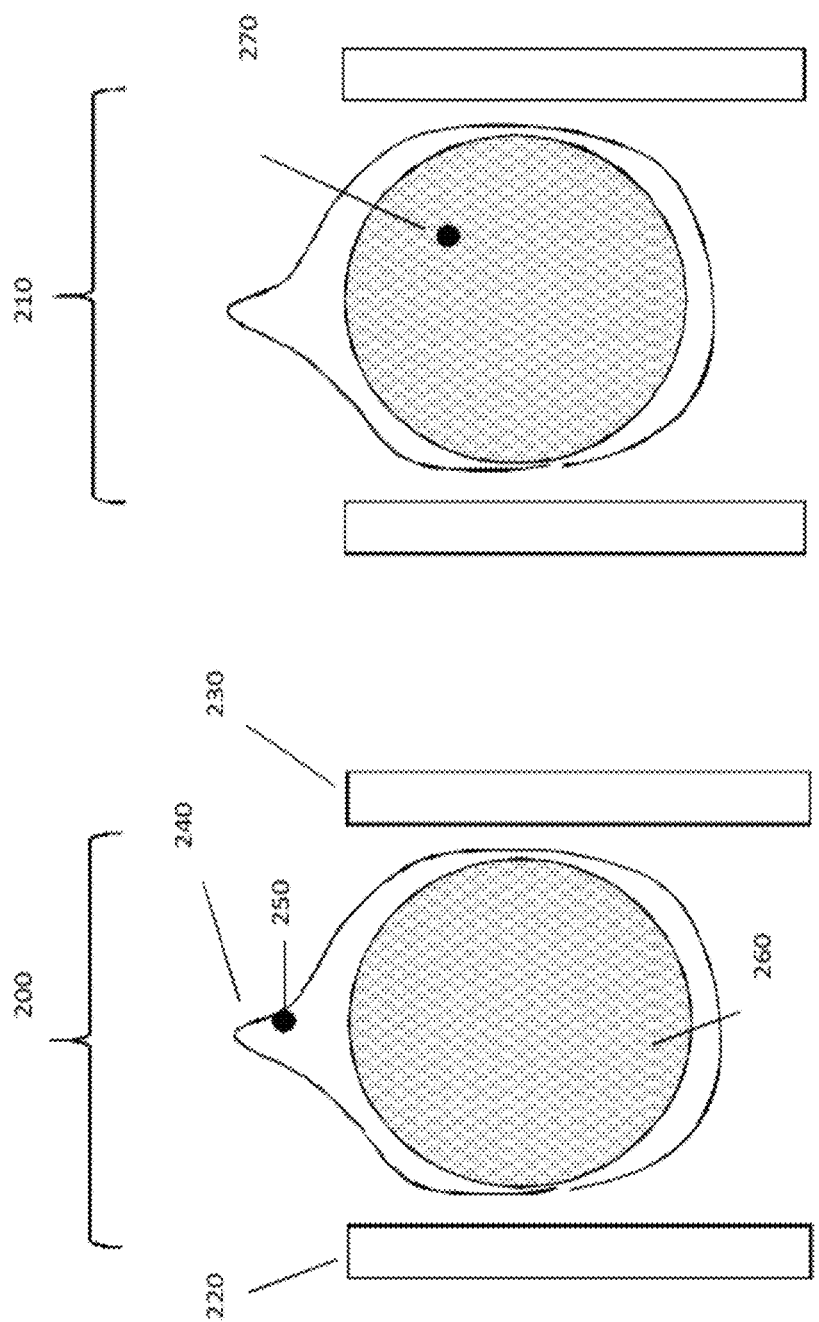
FIG. 2 illustrates an example of equipment provided in accordance with the disclosed embodiments used in combination to deliver an electrical charge to a location in a subject's body.

FIG. 2 illustrates an example of equipment provided in accordance with the disclosed embodiments used in combination to deliver particle 100 to a location in a subject's body. In configuration 200, particle 100 (now called 250 in FIG. 2) is introduced into the nose 240 of the patient's head. The patient's brain is listed as 260. The patient's head is between magnetic sub-systems 220 and 230. Subsystems 220 and 230 are part of an image-guided magnetic delivery system, and in one embodiment may include coils and magnets as described in U.S. Non-provisional patent application Ser. No. 15/427,426 (U.S. Patent Publication 2017/0227617 A1), entitled "METHOD AND APPARATUS FOR MANIPULATING ELECTROPERMANENT MAGNETS FOR MAGNETIC RESONANCE IMAGING AND IMAGE GUIDED THERAPY" (incorporated herein by reference). Magnetic gradients are applied by subsystems 220 and 230 to propel particle (now-called 270) across the cribriform plate and into the brain, as shown in configuration 210 of FIG. 2. It is understood that the magnets used to propel particle 100/250/270 may be of a different configuration than shown in FIG. 2. For example, a magnet may be placed on only one side of the head, or may encircle the head. Subsystems 220 and 230 may represent any type of equipment for controlled generating a magnetic field gradient, e.g., a Magnetic Resonance Imaging (MRI) machine that applies a magnetic field gradient to subatomic particles in tissue to spatially encode a subsequent response from the atoms and molecules in the tissue to a radiofrequency pulse. It is understood that the location of the particle 270 in the brain may be very important to achieve a therapeutic outcome. For example, location 270 may be the nucleus accumbens, an important region for treating addiction. Alternatively, location 270 may be in the peri-acqueductal gray matter, an important region for treating pain. It is also understood that the term "particle" may mean many individual particles, for example one billion. It is understood that the numbers 250 and 270 in FIG. 2 may refer to particles and also to the particle locations, similar to the way that a designation of a country on a map can refer to the location of the country, and to the inhabitants of that country, and to the political structure of that country.

As shown in FIG. 2, operations may include applying a magnetic field gradient at 305 using an MRI device (represented by 220 and 230) to image the tissue in which the particle(s) 100 are positioned. More specifically, MRI device may apply a magnetic field gradient to the subatomic particles in tissue to spatially encode a subsequent response from the atoms and molecules in the tissue to a radiofrequency pulse. Accordingly, this method operation includes detecting an electromagnetic response from the tissue, so as to generate an image of the tissue at least partly based on that response.

Subsequently, or parallel to the application of such a magnetic field gradient, the MRI device (represented by 220 and 230) may be used to control and manipulate operation of the particle(s) themselves at 270, to stimulate at least one neuron within the tissue. Such stimulation may be performed by delivering electrical charge to the tissue by modulating a current applied to the tissue by the particle(s) under the influence of electromagnetic fields applied by the MRI device.

Figure 3:
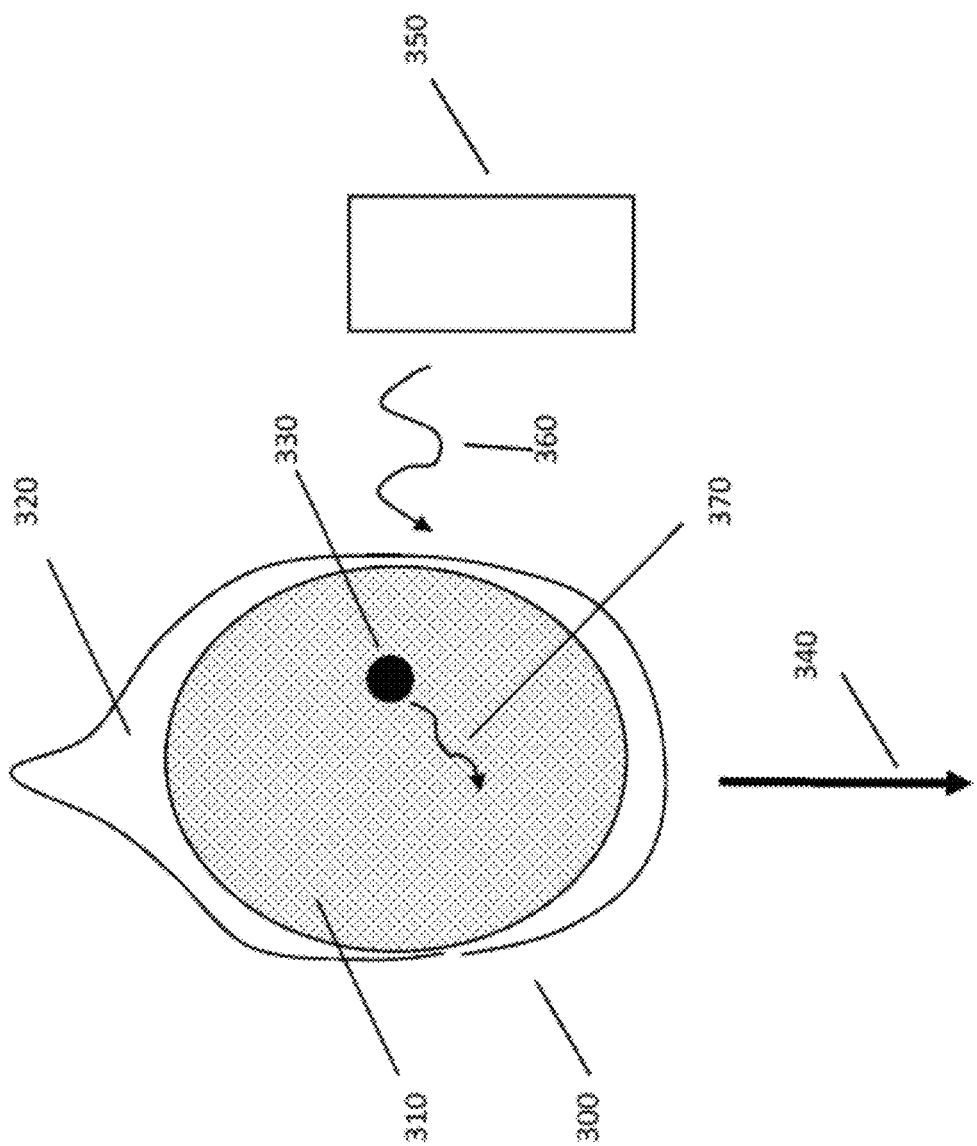
FIG. 3 further illustrates an example of equipment provided in accordance with the disclosed embodiments used in combination to deliver electrical or other energy to a location in a subject's body.

As shown in FIG. 3, the particle(s) (now called 330), having been introduced via nose 320 or other means into brain 310 or other tissue within a subject's body 300, and an emitting device 350 for creating RF electromagnetic wave radiation 360 may be provided and placed in proximity to the subject's body 300, or worn on the human subject's body 300. For example, the device may be placed within a meter of the tissue of interest in the subject's body. That emitting device for creating RF electromagnetic wave radiation 360 may be any device 350 for generating ambient electromagnetic energy for conversion into electrical energy for use by components, e.g., particle(s) 330 included within a human subject's body.

The emitting device 350 may include a magnetic field generator, e.g., a magnetic coil and an RF generator or transmitter. The magnetic coil generates a time-varying magnetic field and the RF generator emits radio waves, and the device may also apply a static magnetic field. The device may include a power source that may be any type of generator suitable for generating power to be provided to the one or more of the components connected thereto. In an embodiment the emitting device may include a magnetoelectric material that does not require a coil to emit electromagnetic or magnetic radiation.

The emitting device 350 may operate under control of a controller included within emitting device 350, or where the controller is separate from 350. Such a controller may be implemented in whole or in part using a computer processor that may be configured assist in performing operations described herein. Accordingly, software code, instructions and algorithms utilized may be utilized by such a processor and may be stored in a memory that may include any type of known memory device including any mechanism for storing computer executable instructions and data used by a processor. Further, the memory may be implemented with any combination of read only memory modules or random access memory modules, optionally including both volatile and nonvolatile memory.

Alternatively, some or all of the emitting device computer executable instructions may be embodied in hardware or firmware (not illustrated). Further, it should be appreciated that, although not illustrated, the controller may similarly be coupled for communication and control to one or more user interfaces that may include display screens, one or more keyboards, and other types of user interface equipment.

As explained above, with regard to spintronic devices, spin-torque can be controlled to drive microwave oscillations can be manipulated and controlled to stimulate tissue in the body using external radiofrequency antennas. For the purpose of this disclosure, STNOs are presented as one component of one enabling configuration. For the purpose of this disclosure, the term "transducer" may be used instead of particle or particles.

Alternatively, or in addition, in accordance with at least one embodiment, the at least one particle may be placed in the at least one desired location in the subject's brain or other part of the body using an image-guided magnetic propulsion technique. Thus, in accordance with at least one embodiment, the at least one particle may be placed at the desired location using manipulation and control of a magnetic gradient. For example, the positioning and placement may be performed under imaging guidance, for example as taught by in U.S. Pat. No. 9,380,959, entitled "MRI-GUIDED NANOPARTICLE CANCER THERAPY APPARATUS AND METHODOLOGY" (incorporated herein by reference).

In at least one embodiment, the at least one particle may be introduced into the body via the nose, and be transported into the nervous system across the cribriform plate. In at least one embodiment, the at least one particle may be introduced into the body via the blood or spinal canal. Since at least one component of the spintronic particle contains magnetic material, the particle may be transported to a location in the body using magnetic gradients. Thus, as taught in the non-provisional patent application Ser. No. 13/761,200 (U.S. Patent Publication 2013/0204120), entitled "EQUIPMENT AND METHODOLOGIES FOR MAGNETICALLY-ASSISTED DELIVERY OF THERAPEUTIC AGENTS THROUGH BARRIERS," (incorporated herein by reference), at least one particle may be placed in the at least one desired location in the subject's brain or other part of the body by image-guided magnetic propulsion. Additionally, the imaging data may be used to accurately position at least one particle in, or in proximity to, tissue including one or more neurons in the subject's body.

Figure 4:
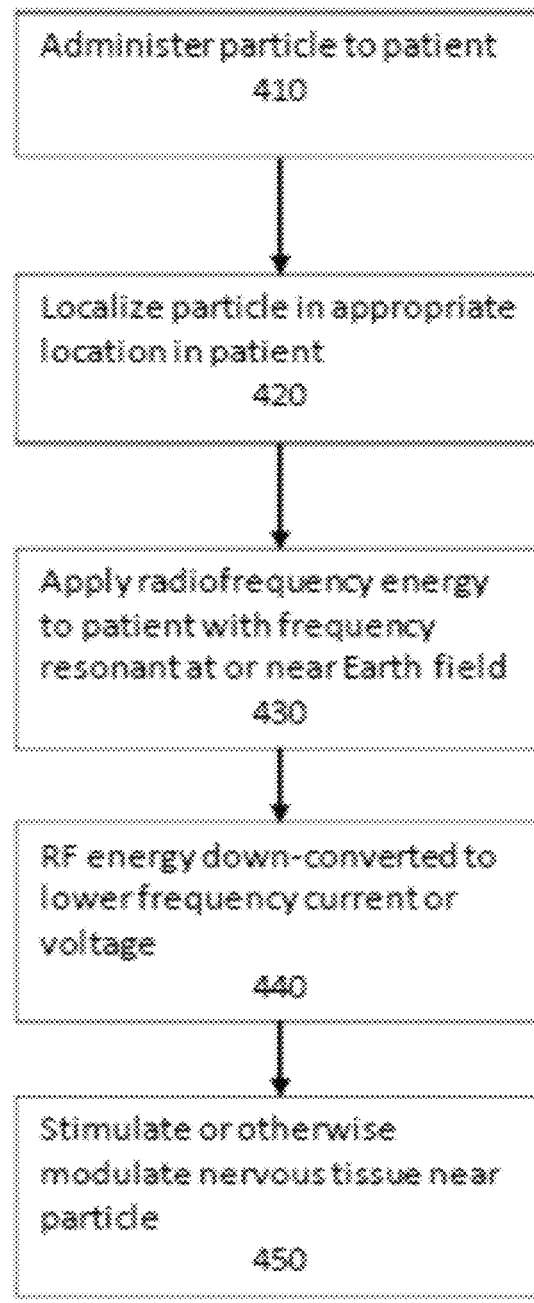
FIG. 4 is a flow-chart of an example of method operations for implanting and activating one or more stimulators within a subject's body performed in accordance with disclosed embodiments.

FIG. 4 illustrates the method of the invention. In the initial step 410, at least one particle is administered to the patient. For example, one billion spintronic particles may be instilled into the nose of the patient under magnetic propulsion to transport the particles into the brain. In step 420, the particles are further propelled under imaging guidance to the appropriate nucleus or other location in the brain. For example, the particles may be localized to the bilaterial nuclei accumbens for a patient with addiction. Following placement of the one or more particles, in step 430 an emitting device is placed near the patient to apply radiofrequency electromagnetic energy to the particles, with a frequency that the particles are sensitive to. For example, the particles may be spintronic particles with a resonant frequency such that the efficiency of transduction is at least 10% higher at the specific frequency of radiation emitted by the device as compared to twice that frequency or half that frequency. In step 440, the particles convert the energy from the higher radiofrequency radiation (for example 1 GHz) to lower frequency electrical current or voltage (for example 10 Hz), since neurons are more sensitive to lower frequency radiation. In step 450, the lower-frequency voltage or current has a beneficial effect (for example stimulation or inhibition) on nervous tissue (for example one or more nerves or neurons) at the location where the particles have been placed. In an embodiment, the effect of the electrical current or voltage is to eliminate or otherwise damage cancer cells. In an embodiment, the effect of the electrical current or voltage is to facilitate delivery of a drug or compound into a tissue or cells, for example by electroporation. It is understood that the term "coupling" means the conversion of radiation incident on the functional particle to an action performed by the particle on tissue in the subject's body.

In accordance with at least one embodiment, the particle(s) 100 may be coated with a material that eases entry into certain locations in the subject's body, for example, particle 100 may be coated with a lipophilic material to aid entry from a vessel across the blood brain barrier into the brain. Such a strategy is taught by R. C. Van Lehn and A. Alexander-Katz in the article entitled: "FREE ENERGY CHANGE FOR INSERTION OF CHARGED, MONO-LAYER-PROTECTED NANOPARTICLES INTO LIPID BILAYERS," Soft Matter, vol. 10, no. 4, p. 648, Dec. 2014 (incorporated by reference in its entirety).

In accordance with at least one embodiment, particle 100 may be coated with a material to reduce toxicity, for example an L1 coating as taught by C. L. Kolarcik, et al in the article entitled: "IN VIVO EFFECTS OF L1 COATING ON INFLAMMATION AND NEURONAL HEALTH AT THE ELECTRODE-TISSUE INTERFACE IN RAT SPINAL CORD AND DORSAL ROOT GANGLION," *Acta Biomater.*, vol. 8, no. 10, pp. 3561-75, Oct. 2012 (incorporated herein by reference).

In accordance with at least one embodiment, the particle(s) 100 may be coated with a material to attract or retain the particle in or near a specific type of neuron, or in or near a structure of a neuron (for example, straddling the neuronal membrane).

Control then proceeds to 410, at which that device for creating RF electromagnetic wave radiation generates ambient electromagnetic energy for conversion into electrical energy for use by the particle(s) included within a human subject's body. Note, the creation of the RF electromagnetic wave radiation may be performed under control of a controller, which may be implemented via hardware and software components, as explained herein.

In accordance with at least one embodiment, the above-described equipment and methodologies can be used to provide medical therapy for, and a brain machine interface that alters and/or diagnoses and or improves biological, cognitive, and/or mood related brain operation for various conditions, including Parkinsonism and depression. Additionally, the equipment and methodologies may provide such functionality for treating addiction by having the patient undergo image-guided implantation of the at least one particle in a region of the brain responsible in part for addiction, for example, the nucleus accumbens, as taught by J. Kuhn et al in the article entitled "DEEP BRAIN STIMULATION OF THE NUCLEUS ACCUMBENS AND ITS USEFULNESS IN SEVERE OPIOID ADDICTION," *Mol. Psychiatry*, vol. 19, no. 2, pp. 145-146, Feb. 2014 (incorporated herein by reference).

Technical utility is provided at least in that a subject may receipt electrical stimulation of neurons after implantation as a result of the subject wearing a device that emits RF electromagnetic waves at a frequency to which implanted particles are sensitive at the earth's magnetic field, so as to cause stimulation or modulation of neurons near the particle.

It should be understood that the presently disclosed embodiments also provide a method that can be used to treat pain in other regions of the body that are innervated, by delivering particles to nerves causing the pain, and then stimulating or modulating the nerves.

Other conditions may be treated similarly by delivering particles to important locations, for example, neurodegnerative disease, memory loss, and some psychiatric disorders.

Further, disclosed methodologies can treat cancers by delivering electrical current or voltage that can kill cells or keep them from reproducing.

While disclosed embodiments have been described in conjunction with the specific embodiments outlined above, it is evident that many alternatives, modifications and variations will be apparent to those skilled in the art. Accordingly, the various embodiments of the invention, as set forth above, are intended to be illustrative, not limiting. Various changes may be made without departing from the spirit and scope of the invention.

For example, in accordance with at least one embodiment, it should be understood that the presence of synchronized multiple particles may add to the effectiveness of stimulating the tissues. Further, it should be understood that many particles can be used, which may be concentrated in a specific location by magnetic focusing techniques, for example dynamic inversion as described in U.S. Pat. No. 9,694,196 entitled "SYSTEM, METHOD AND EQUIPMENT FOR IMPLEMENTING TEMPORARY DIAMAGNETIC PROPULSIVE FOCUSING EFFECT WITH TRANSIENT APPLIED MAGNETIC FIELD PULSES" (incorporated herein by reference).

Further, as explained briefly above, in an embodiment, the device used to magnetically focus the particles disclosed herein may also be used to image the brain and the particles. For example, in accordance with at least one embodiment, a system may be provided in or work in combination with an MRI device alters the static magnetic field of the focusing device in less than one minute with the use or electropermanent magnets or other means, as taught in U.S. Nonprovisional patent application Ser. No. 15/427,426 (U.S. Patent Publication 2017/0227617), entitled "METHOD AND APPARATUS FOR MANIPULATING ELECTROPERMANENT MAGNETS FOR MAGNETIC RESONANCE IMAGING AND IMAGE GUIDED THERAPY" (incorporated by reference).

It should also be understood that the particles can, optionally, have features that improve transport, for example with rings that allow spinning as taught by L Mair et al in U.S. Non-provisional patent application Ser. No. 14/930,126 (U.S. Patent Publication 2017/0069416), entitled "METHOD AND APPARATUS FOR NON-CONTACT AXIAL PARTICLE ROTATION AND DECOUPLED PARTICLE PROPULSION" (incorporated herein by reference).

In accordance with at least one embodiment, it should be understood that the particle may be coupled to some other material or combination of materials that may be used to sense voltages or currents from the nearby neuron. An example of such material is disclosed in U.S. Provisional Patent Application 62/490975, entitled "APPARATUS AND METHOD FOR REMOTE DETECTION OF ELECTRIC FIELDS IN LIVING TISSUES USING MAGNETIC PARTICLES AND LIQUID CRYSTALS" (incorporated herein by reference).

In accordance with at least one embodiment, the spintronic particle itself may be used to assess currents or voltages in or near a neuron, as described in U.S. Non-Provisional patent application Ser. No. 14/632,982 (U.S. Patent Publication 2015/0238110), entitled "NEUROPARTICLE WITH A SPIN-TORQUE DEVICE" (incorporated herein by reference).

Additionally, it should be understood that the functionality described in connection with various described components of various embodiments may be combined or separated from one another in such a way that the architecture of the resulting system is somewhat different than what is expressly disclosed herein. Moreover, it should be understood that, unless otherwise specified, there is no essential requirement that methodology operations be performed in the illustrated order; therefore, one of ordinary skill in the art would recognize that some operations may be performed in one or more alternative order and/or simultaneously.

Various components of the invention may be provided in alternative combinations operated by, under the control of or on the behalf of various different entities or individuals.

Further, it should be understood that, in accordance with at least one embodiment of the invention, system components may be implemented together or separately and there may be one or more of any or all of the disclosed system components. Further, system components may be either dedicated systems or such functionality may be implemented as virtual systems implemented on general purpose equipment via software implementations.

As a result, it will be apparent for those skilled in the art that the illustrative embodiments described are only examples and that various modifications can be made within the scope of the invention as defined in the appended claims.

What is claimed:

1. An apparatus comprising:
   at least one emitting device positioned near a human subject and generating electromagnetic radiation; and
   at least one functional particle whose action is sensitive to the frequency of the electromagnetic radiation emitted by the at least one emitting device,
   wherein the at least one functional particle converts incident electromagnetic radiation into electrical current or voltage with an efficiency that depends on a surrounding magnetic field strength,
   wherein said magnetic field is Earth's magnetic field,
   wherein the at least one emitting device is configured to be located within 1 meter of tissue in a body of the subject and outside the subject's body,
   wherein the at least one functional particle is configured to be located inside the subject's body, and
   wherein the electrical current or voltage has an effect upon tissue within the subject's body.

2. The apparatus of claim 1, wherein the subject's body tissue contains electrically-active cells.

3. The apparatus of claim 2, wherein the electrically-active cells include neurons.

4. The apparatus of claim 1, where the at least one functional particle is a transducer configured to receive radio-frequency energy from the electromagnetic radiation and transduce the received radio-frequency energy into current or voltage that is at a lower frequency than the received radio-frequency energy, and wherein the transduction is configured to produce a lower-frequency current or voltage to effect tissue within the subject's body.

5. The apparatus of claim 1, where the at least one emitting device is under control of a controller.

6. The apparatus of claim 1, further comprising a magnetic resonance imaging system through which a static magnetic field is altered in less than one minute, whereby the at least one functional particle is transportable under imaging guidance using the magnetic resonance imaging system.

7. The apparatus of claim 1, wherein the subject's body tissue contains cancer cells.

8. The apparatus of claim 1, wherein an efficiency of transduction is at least 10% higher when the patient is exposed to the Earth's magnetic field as when the patient is exposed to a magnetic field that is twice as high or twice as low as the Earth's magnetic field.

9. The apparatus of claim 1, wherein the at least one functional particle is a spintronic device.

10. A method of affecting tissue in a subject's body, the method comprising:
    propelling at least one functional particle to a desired location in a human subject's body under imaging guidance,
    wherein the at least one functional particle is most efficient at coupling energy at or near a specific frequency at Earth's magnetic field, and
    subsequently generating electromagnetic or magnetic radiation at said specific frequency from an emitting device placed within one meter of the subject's body; and
    wherein the at least one functional particle converts incident electromagnetic radiation into electrical current or voltage with an efficiency that depends on a surrounding magnetic field strength,
    and the electrical current or voltage has an effect on tissues in the subject's body.

11. The method of claim 10, where a function of the at least one functional particle is configured to convert energy from the incident electromagnetic radiation to energy at a lower frequency.

12. The method of claim 10, wherein the tissues of the subject's body contains electrically-active cells.

13. The method of claim 12, wherein the electrically-active cells include neurons.

14. The method of claim 10, further comprising altering operation of a magnetic resonance imaging system which generates a static magnetic field in less than one minute, whereby the at least one functional particle is transportable under imaging guidance using the magnetic resonance imaging system.

15. The method of claim 10, wherein the tissue in the subject's body contain cancer cells.

16. The apparatus of claim 10, wherein an efficiency of transduction is at least 10% higher when the subject's body is exposed to the Earth's magnetic field as when the subject's body is exposed to a magnetic field that is twice as high or twice as low as the Earth's magnetic field.

17. The method of claim 10, wherein the at least one functional particle is a spintronic device.

18. The method of claim 10, further comprising transporting the at least one functional particle to tissue at a location in the subject's body using magnetic gradients.

19. The method of claim 18, wherein the at least one functional particle is transported under imaging guidance.

20. The method of claim 10, further comprising introducing the at least one functional particle is introduced into the subject's body non-invasively.

21. The method of claim 20, wherein the at least one functional particle is introduced into the subject's body via the subject's nose.

22. The method of claim 10, further comprising concentrating a plurality of functional particles, including the at least one functional particle, at a location in the subject's body using dynamic inversion.

23. The method of claim 10, wherein a function of the at least one functional particle is to electroporate cells.

24. The method of claim 10, wherein a function of the at least one functional particle facilitates entry of drugs or compounds or other materials into cells or tissues.

\* \* \* \* \*